United States Patent [19]

Butterworth et al.

[11] Patent Number: 4,466,552
[45] Date of Patent: Aug. 21, 1984

[54] STERILIZATION CONTAINER FORMED OF NONWOVEN MATERIAL

[75] Inventors: George A. M. Butterworth, Wilbraham, Mass.; William M. Evans, Mundelein; Howard J. Goldner, Highland Park, both of Ill.

[73] Assignee: American Hospital Supply Corporation, Evanston, Ill.

[21] Appl. No.: 520,992

[22] Filed: Aug. 8, 1983

[51] Int. Cl.³ ............................................. B65D 43/06
[52] U.S. Cl. .................................... 220/354; 220/306; 206/439
[58] Field of Search ....................... 220/306, 307, 354; 206/439, 370

[56] References Cited

U.S. PATENT DOCUMENTS 4,124,141 11/1978 Armentrout et al. ............... 220/306
4,228,916 10/1980 Weingardt .......................... 220/354

Primary Examiner—George T. Hall
Attorney, Agent, or Firm—Emrich & Dithmar

[57] ABSTRACT

A sterilization container for holding medical or surgical items during steam (or gas) sterilization procedures is formed entirely of resin-treated nonwoven material which provides a bacterial filter. The container includes a tray and a cover having correspondingly shaped seal flanges formed to provide a double seal and a tortuous path establishing a bacterial barrier. The lid and tray each have body portions adapted to be firmly gripped or handled with separate hands and the body portions are spaced from and related to the seal flanges in such a manner that the sterilized container may be opened and its contents presented or dispensed while maintaining sterile technique. The container is soft yet semi-rigid even after being subjected to steam sterilization. Ribbing on the bottom surface of the tray provides for strength, raises the contents above any collected condensate, promotes circulation of steam during sterilization to all surfaces of the item supported by the ribs, and promotes ventilation of air about the item after sterilization. The top surface of the cover may be similarly ribbed.

17 Claims, 5 Drawing Figures

STERILIZATION CONTAINER FORMED OF NONWOVEN MATERIAL

BACKGROUND OF THE INVENTION

The present invention relates to apparatus for use in sterilization of surgical or medical items such as surgical instruments and prosthetic devices. In particular, the present invention relates to a sterilization container suitable for use in conventional steam (i.e., autoclave) or flash sterilization procedures currently used in hospital and surgical techniques for establishing and maintaining sterile conditions for these instruments and devices (collectively referred to as "medical items").

There are a number of different processes for sterilizing medical items which are recognized in the industry as effective, for example, steam sterilization or exposure to radiation or a gas. Even for a given sterilization process, the procedure for effecting sterilization may vary according to the apparatus used.

By way of example, conventional steam (i.e., autoclave) sterilization is widely used in hospital central supply areas where time is not critical. This procedure requires exposure to steam at 250° F. for at least 15 minutes. So-called "flash" sterilization which is more commonly used in operating rooms, subjects the items to higher temperatures (e.g., 270° F.) for a shorter time (three minutes or more) according to well-known and accepted data relating sterilization to these parameters. Another technique, exposure to ethylene oxide (88/12) at a temperature of 120°-140° F. and 20-40% R.H. for a minimum of one hour is also used and is an accepted method for sterilizing medical items.

If the intended use of the sterilized item is in an operating room where flash sterilization is most commonly used, the items and their containers are normally not wrapped, so they may still be hot when it is desired to retrieve or transfer them, thereby requiring special safety procedures for handling.

Other items, such as instruments used frequently or regularly, may be subjected to conventional steam sterilization before their intended use and then stored in a central supply facility. In such a case, provision must be made for maintaining until use the sterile condition that has been achieved.

If it is desired to maintain sterility for some storage period, after conventional steam sterilization, the tray and contents may be wrapped prior to sterilization with a steam-permeable material such as linen or disposable sterilization wrap which will serve as a bacterial filter after sterilization and during storage. Sometimes the surgical item is wrapped separately and placed in the tray, and then the entire tray and contents are wrapped again. Typically, strips of tape are applied to the fully wrapped tray and contents, and dated in some cases, so that supply personnel will know that the parcel has been sterilized and when it was sterilized.

One disadvantage of applying a sterilization wrap is that it may tear or be punctured in handling, thereby violating the sterility of the contents. This is particularly true in the use of metal trays which are containers most widely used currently. In storage, for example, the trays are sometimes slid along metal shelves which contribute to the problem of tearing the wrap.

Another sterilization technique for central supply employs specially designed reusable containers of stainless steel or aluminum which have sealable lids. Although reusable containers provide an impervious barrier to bacteria after sterilization, holes or channels must be provided to admit steam during the process. These holes or channels must be covered with sterilization wrap to prevent contamination. Sometimes mechanical valves are provided which are opened during sterilization and closed thereafter. Because of the impermeability the chance of undesirable water accumulating within the container is increased. Thus, the term "reusable" refers to the fact that the container, which does not require a complete wrap prior to each sterilization, is reusable, although any wrap or filter and even some valves are discarded after use.

A wide variety of apparatus is available for use for sterilizing medical items. Where flash sterilization is employed, typically open stainless steel trays having perforated or metal mesh bottoms are used. These trays are also suitable for complete wrapping with a sterilization wrap and storage in a central supply area. Other apparatus available for use in central supply areas includes a metal container with closable top having both top and bottom perforated for steam penetration.

So-called reusable containers may have an impermeable tray and hinged cover adapted to be closed and thereby seal the contents to obviate the use of a sterilization wrap. A valve may be opened to admit steam during sterilization procedure and then closed to seal the sterilized environment within the container. Alternatively, an opening is provided in the container with a replaceable filter which provides a bacterial barrier during storage.

There are a number of disadvantages associated with the systems and apparatus described above which are currently used to sterilize medical items. One of the more common disadvantages with the apparatus is that of weight. Metal trays, whether stainless steel or aluminum, are heavy. The added weight of instruments makes these trays even more difficult in handling and manuevering.

A second disadvantage is the special precautionary handling procedures required for flash sterilization. Metal has a high heat capacity and the temperature of metal sterilization trays remains high following sterilization. Clamps or cushioned heat pads must be used in handling them immediately following steam sterilization, as previously mentioned. Further, because of the high heat capacity of the trays, they remain cooler than other materials during steam sterilization, and thereby form water condensate for a longer period of time. Condensate may accumulate either in the bottom of the tray, if it is not of the screen mesh type, or, depending upon the shape and nature of the items being sterilized, moisture may accumulate in or on one or more of the items.

Further, where commercially available sterilization wrap is used to completely enclose metal trays, it is susceptible to tearing or puncture, thereby violating the sterility that may have been achieved. This disadvantage is particularly apparent, as mentioned, where a previously-sterilized tray and its contents are stored for later use in a central supply area where handling is likely to be more rough than in an operating room and the wrapped tray is subject to sliding on metal shelving.

The shelf life of a wrapped tray is limited, typically of the order of 30 days. This is considered too short a time for certain items which are infrequently used, thereby requiring special procedures for such items to insure their sterilization prior to use.

Another disadvantage of metal trays having perforated or mesh bottoms is that even stainless steel is subject to corrosive attack or oxidation in the extremely hostile environment of repeated exposure to steam at elevated temperatures.

Reusable container systems, while obviating some of the problems of wrapped trays, have created still further problems. For example, reusable container systems are normally heavier than simple perforated trays. The added weight, of course, makes them more cumbersome in handling and maneuverability. In addition, however, the procedures required for sterilization are considered by some to be too complex, requiring mechanical valves or inserted wrap for use as filters, or other special procedures or techniques depending upon the apparatus. Any one of these special procedures or devices could cause malfunction or simply be forgotten, thereby causing a failure of sterility.

Reusable systems also typically require a large initial investment for a hospital and considerable preliminary evaluation and justification, both from financial and efficacy stantpoints, prior to purchase and installation. Further, due to high manufacturing costs, reusable containers are available only in limited sizes.

Again, depending upon the apparatus of the particular sterilization system, if it is reusable particularly, a new system of this type may require retraining of personnel.

SUMMARY OF THE PRESENT INVENTION

The present invention provides a sterilization container for holding medical or surgical items which is particularly suited for use in all currently used sterilization processes and which overcomes many of the problems associated with conventional metal trays or reusable containers.

The container of the present invention includes a tray and a cover, both of which are made entirely of resin-treated nonwoven material which provides the bacterial barrier, yet is readily permeable to steam and provides a complete spherical line-of-sight permeability for steam or gas. The nonwoven material is formed into the desired shapes of the respective lid and tray. The container is semi-rigid and will retain its shape under normal use conditions. It is inexpensive enough that it may be discarded after use. The nonwoven material is more resistant to tearing and puncture than commercially available sterilization wrap.

The tray and cover have correspondingly-shaped seal flanges formed to provide a double seal of a large contact area. The seal is in the form of serpentine or curved cusps located in tandem so as to provide a tortuous path establishing a bacterial barrier. In addition to providing a bacterial barrier, the large area of the seal creates a frictional coupling between the cover and tray to prevent accidental separation of the two.

The tray of the illustrated embodiment is generally rectangular in horizontal cross-section, and the bottom of the tray is ribbed. In addition to providing strength, the ribs provide raised inner surfaces for holding the items being sterilized and preventing their continued contact with regions of collected moisture. They also enhance circulation of steam during sterilization and promote ventilation and drying of all surfaces of the item after sterilization.

The tray includes four side walls which are inclined upwardly and slightly outwardly. The upper edges of the side walls extend outwardly to provide the sealing flange of the tray.

Similarly, the cover of the container includes a longitudinally-ribbed top wall and four side walls which depend downwardly and slightly outwardly. A continuous peripheral sealing flange is formed at the bottom of the side walls of the lid. Recesses are formed in the top of the cover for placement of thumbs in retrieving or carrying the container.

In dispensing the sterilized items or in presenting them for use, for example from a circulating nurse to a scrub nurse, the entire tray and contents are removed from the sterilization apparatus, and one hand grips the tray by straddling the bottom wall and engaging opposing side walls while the other hand similarly straddles the top wall of the cover and engages opposing side walls of the cover between the thumb and fingers. The container is then opened by pulling the cover upward and away from the tray to break the serpentine seal. When this procedure is followed, the hands of the presenter are fixed relative to the tray and cover; and the hands are remotely located from the sterile edge, with no likelihood of crossing that edge, thereby maintaining sterile technique.

The present invention thus provides a single structure which overcomes the major problems existing in current apparatus used in both flash sterilization and autoclaving. Because it is non-metalic, the present container can be handled immediately after flash sterilization and even acts to isolate the hands from the sterilized item which may be metal and still hot. Because it provides a self-contained, fully closed and sealed bacterial barrier after sterilization, it obviates the need for sterilization wrap or special procedures where it is desired to store the sterilized item for future use.

A principal advantage of the present invention over existing commercial apparatus is the light weight of the tray. Despite the light weight, however, the inventive tray is capable of carrying relatively heavy instruments without bending or collapsing.

By employing nonwoven material for both the tray and the lid, there is a straight line-of-sight path for steam through the container from every angle since the nonwoven material is permeable to steam. This facilitates sterilization and may ultimately reduce the time required to achieve sterilization. The use of nonwoven material has the further advantage that it can be handled without fear of burning almost immediately after the sterilization process, yet it retains its semi-rigid structural integrity following sterilization. Another advantage of the present invention is that there is no likelihood of corrosion that might otherwise occur in the use of metal sterilization trays when the metal of the tray is different from the metal of the instrument or article being sterilized. Obviously, the nonwoven material itself is not subject to corrosion (as in the case of metal sterilization trays) despite the length of time or the degree of steam temperature used.

The light weight bacterial barrier properties, and low heat capacity of the nonwoven sterilization container of the present invention provides opportunities for new sterile technique management methods. For example, it is expected that testing will ultimately establish that a sterile environment can be maintained for an extended period of time if the seal between cover and tray is not broken, or that requirements for sterile presentation by the circulating nurse to achieve aseptic transfer may be reduced due to the maintainence of the sterile edge on both the lid and the tray holding the surgical instrument during and after presentation.

The nonwoven material used to form both the tray and the lid are preferably treated to be fluid repellant; and these desirable characteristics are retained after sterilization. Another advantage inherent in the use of nonwoven materials is that they maintain no static electrical charge, and this is an important safety feature particularly in surgical suite usage.

To summarize the advantages of the container of the present invention over prior trays requiring the application of exterior sterilization wrap, it is lighter, more maneuverable, more resistent to puncture or tearing, and is capable of being removed from sterilization apparatus without heat pads or special handling procedures. It also does not require a large initial expenditure to implement the system; and it is believed that the instant tray is capable of extending the shelf life of sterilized items beyond that now accepted for wrapped trays. The instant container may be provided in a wide variety of sizes or shapes, and may be adapted for use with auxiliary trays or special inserts for sharp or delicate instruments.

With respect to so-called reusable systems, the light weight and reduced initial cost of the present invention are even more pronounced. The present container also affords advantages of simplicity and reduced tendency of human error. Since the nonwoven container material possesses properties that make it an excellent bacterial barrier, it enables a much simpler procedure for assembly and obviates the need for special valves or filters. Of particular importance is the fact that if properly handled, the present container prevents possible contamination in opening of the container and presentation of its contents.

Because of its shape and structural integrity, the present container can be stacked, thereby affording storage efficiency after use; and the trays and covers may be nested for efficient use of space in shipment and pre-use storage.

Other features and advantages of the present invention will be apparent to persons skilled in the art from the following detailed description of a preferred embodiment accompanied by the attached drawing, wherein like reference numerals will refer to identical parts in the various views.

DETAILED DESCRIPTION OF THE DISCLOSED EMBODIMENT

Figure 1:
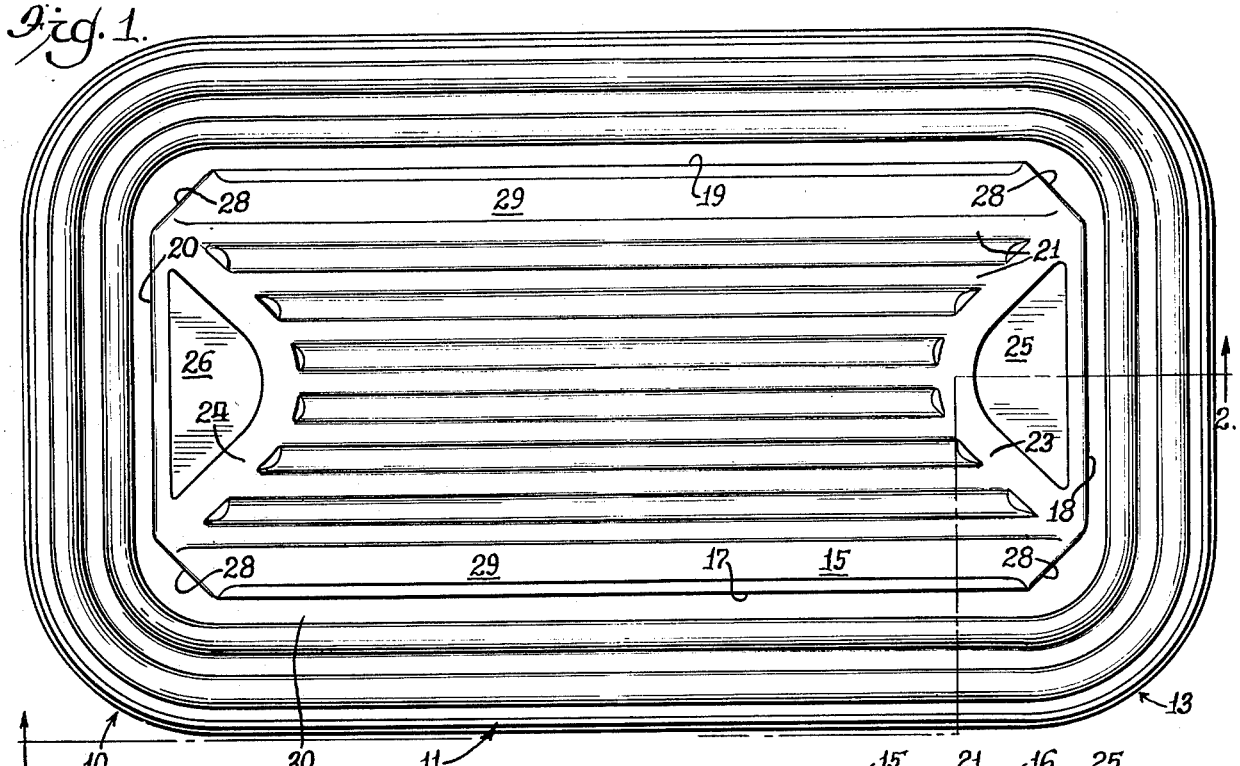
FIG. 1 is a plan view of a sterilization container constructed according to the present invention.
Figure 2:
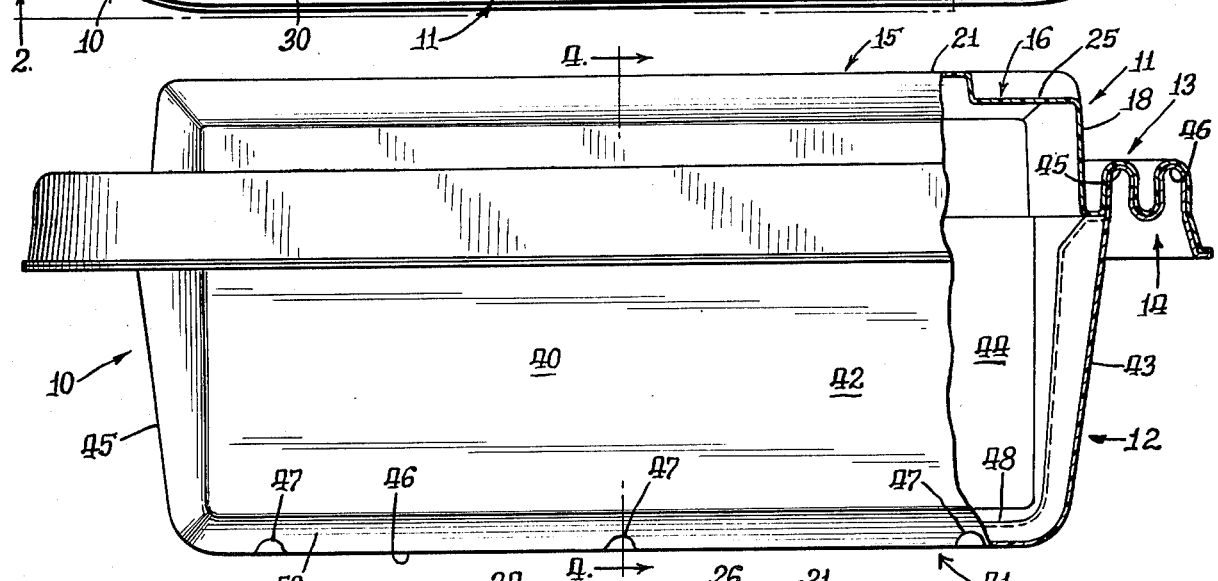
FIG. 2 is a side view of the container of FIG. 1 looking at the longer side and partly sectioned to show the serpentine double seal between the cover and the tray.
Figure 3:
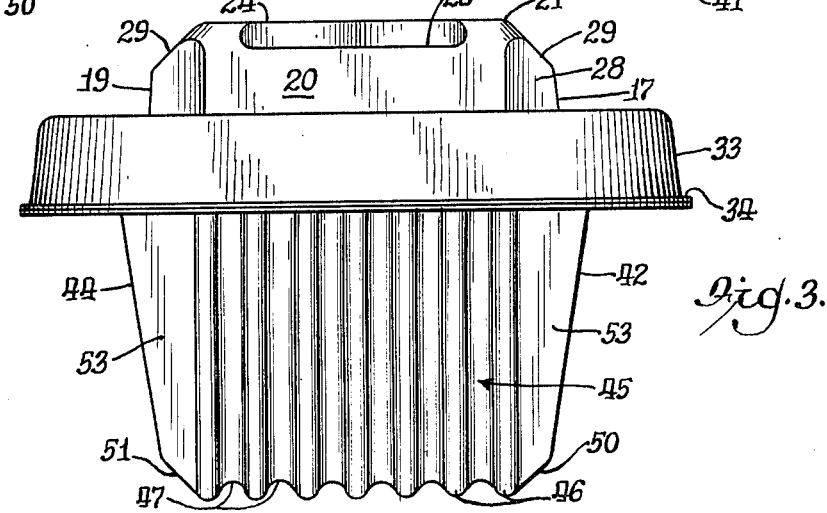
FIG. 3 is an end view of the container of FIG. 1 showing the cover and tray in assembled relation.

Referring first to FIG. 1, a container generally designated 10 includes a cover 11 and a tray or bottom 12. The cover 11 includes a seal flange generally designated 13 and having a doubly curved or serpentine shape in cross-section. Similarly, the upper portion of the tray 12 has a correspondingly shaped seal flange generally designated 14. The seal flanges 13, 14 extend completely and continuously around the peripheries of the cover 11 and tray 12 respectively, as best seen in FIG. 1. When the cover and tray are placed in assembled relation, as seen in FIGS. 2 and 3, the correspondingly shaped seal flanges 13 and 14 engage each other continuously and thereby form a seal and define a tortuous path providing a bacterial barrier.

The cover 11 and tray 12 are formed substantially entirely of formed nonwoven material. As used herein, the term "nonwoven" is used in the sense that the term is understood by persons skilled in the hospital supply industry. In particular, the term refers to a nonwoven fabric or web of continuous filaments—e.g., polyester—which is permeable to air or steam but prevents the transmission of bacteria, as distinguished from a woven fabric which has a comparatively large pore size, a nonwoven has a larger number of much smaller pore with no line-of-sight porosity. It is this structure which permits steam penetration but prevents entry of bacteria. The term may also include standard long textile fiber nonwovens or paper-derived nonwovens capable of providing a barrier to bacteria.

The nonwoven web or fabric is treated with a resin (e.g., a water soluble epoxy, acrylic, phenolic or polyester resin) which remains partially cured until the resin-treated material is placed in a mold formed to the desired shape and heat-treated. The application of heat completes the cure of the resin, and the material takes on the shape of the mold and remains semi-rigid. The article retains its semi-rigid structure even after steam sterilization, yet remain porous and readily permeable to steam.

One suitable material is commercially available and sold under the designation "800621" by The Technical Fabrics Division of Albany International of Auburn, Me. Other nonwoven materials having these structural characteristics together with the ability to provide a bacterial barrier may equally well be employed.

Turning now to the structure of the illustrated embodiment, the cover 11 includes a raised center portion or body generally designated 15 which is inwardly of and completely surrounded by the peripheral serpentine seal flange 13. The body 15 of the cover 11 includes a top 16 and four downwardly and generally outwardly depending side walls 17–20.

The top 16 of the cover 11 is ribbed as at 21 for strength since the overall length of the body 15 (the left-to-right dimension in FIG. 1) may be nominally 10 in. In the illustrated embodiment there are seven such ribs, separated by six troughs or grooves 22; and the end portions of the longitudinal ribs 21 are integrally formed with and extend into generally V-shaped end ribs 23, 24 which extend toward each other and are symmetrical relative to the longitudinal center line of the cover. The end V-rib 23 defines a thumb or finger recess 25 adjacent the top of end wall 18 which may be at substantially the same level as the depth of the grooves 22 (see FIG. 2). A similar thumb recess 26 is formed by the V-rib 24 adjacent the opposing end wall 20, as best seen in FIG. 1. The thumb recesses facilitate handling.

For additional rigidity and crush resistance, the corners of the body 15 of cover 11 are beveled as at 28 as best seen in FIGS. 1 and 3, and the outboard edges of the outermost ribs 21 are canted downwardly and outwardly as at 29.

The structure and function of the peripheral seal flange 13 (which are similar and complementary to seal flange 14) will now be described. The shape of the seal flange 13 in respect of the double serpentine seal is similar throughout the periphery of the cover, and need be described only once. The bottom edges of the side walls 17-20 of the body 15 are formed into a horizontal, outwardly-projecting land 30 which extends about the entire periphery of the body 15. The peripheral flange 13 is then formed integrally with the peripheral outer edge of the land 30. The sealing flange 13 includes inner and outer sealing cusps designated respectively 31 and 32 in FIG. 4 for effecting a double seal. The outer surface of the outermost cusp 32 extends downwardly and is flared slightly outwardly to provide an overhang 33; and the lowermost edge of the overhang 33 extends horizontally outwardly to define an outermost peripheral flange 34.

Figure 4:
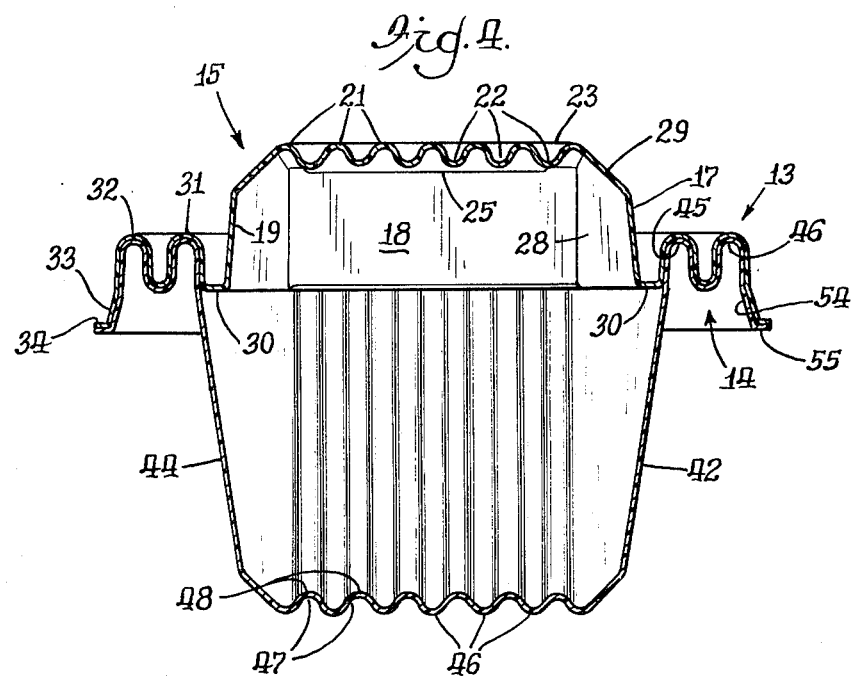
FIG. 4 is a transverse vertical sectional view of the apparatus of FIG. 1 taken along the sight line 4—4 thereof.

Turning now to the detailed structure of the tray 12 of the illustrated embodiment, and with particular reference to FIGS. 2, 3 and 4, it includes a body portion 40 formed integrally with the peripheral seal flange 14 and including a bottom 41 and four generally upright and slightly outwardly inclined side walls 42-45. Opposing side walls 42, 44 are longer than the other pair of opposing side walls 43, 45.

The bottom wall 41 is formed into seven longitudinally extending ribs 46 which may extend up the smaller pair of opposing side walls 43, 45 (see FIG. 3). Cross ribs 47 may be formed in the longitudinally extending ribs 46 for bracing the longer ribs. The spaces between the ribs 46 take the form of grooves when viewed from the outside, but the upper inside surfaces of the grooves 47 (see 48 in the cutaway section of FIG. 2) are raised above the bottom of the ribs 46 and serve to support the item being sterilized while maintaining the item free of contact with any moisture that may have collected at the bottom of the tray.

The outboard edges of the two outermost ribs 46 are joined with inclined bottom wall portions 50, 51 (see FIGS. 3 and 4) which, in turn, are joined to the lower edges of the side walls 42, 44 respectively. The corners between adjacent side walls 42-45 of the tray 12 are also inclined as at 53 (FIG. 3) to brace the walls and provide structural integrity to the tray.

Turning now particularly to FIG. 4, the side walls 42, 44 extend upwardly to the land 30 of cover 11, and above that location, form the peripheral seal flange 14 which includes inner and outer sealing cusps 45, 46 conforming in shape to, and continuously engaging, the serpentine portions 31, 32 respectively of the peripheral seal flange 13 of the cover. Similarly, the end walls 43, 45 of the tray extend into continuations of the inner and outer curved seals 45, 46, as best seen in the case of side wall 43, in FIG. 2. The peripheral lower edge of the outer sealing cusp 46 of the flange 14 is inclined downwardly and slightly outwardly at 54 to provide an overhang corresponding to and contacting the previously-described overhang 33 of the cover; and the overhang 54 has its lower peripheral edge formed horizontally outwardly into a flange at 55.

Figure 5:
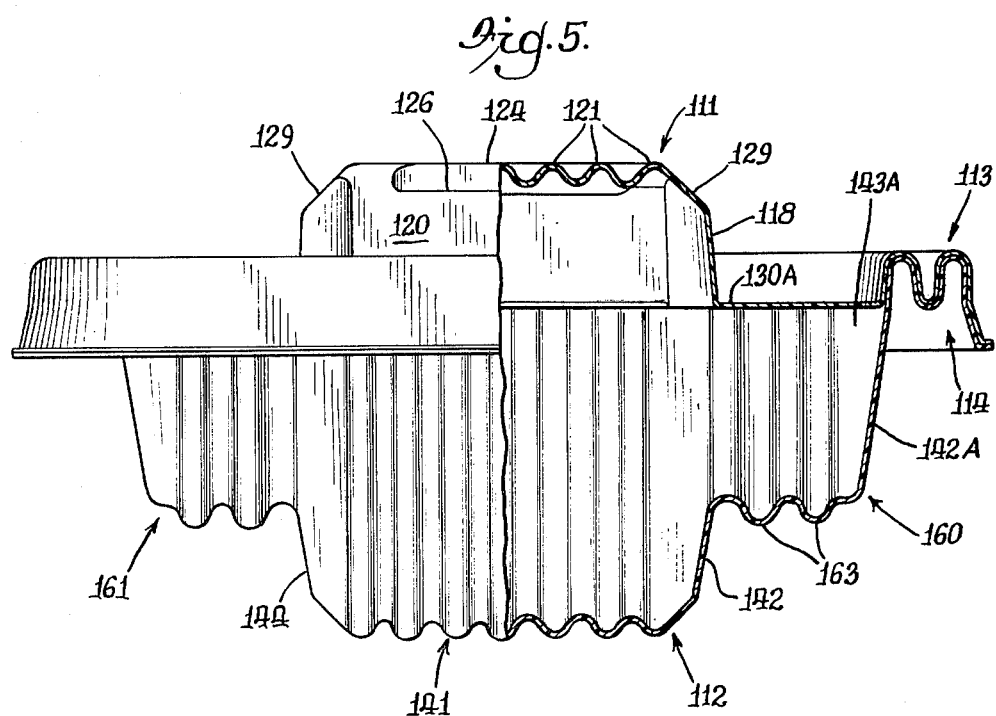
FIG. 5 is an end view of an alternate embodiment of apparatus constructed according to the present invention, again with a portion sectioned away to show the cover and tray in assembled relation.

In an alternate embodiment adapted to hold larger instruments during sterilization than the embodiment just described is capable of holding, reference is made to FIG. 5 which is a partially sectioned end view. In this embodiment, elements or structure similar to that already disclosed in connection with the first embodiment bear similar reference numerals preceded by the numeral "1"—thus, the cover is designated 111, and the tray 112. In this alternate embodiment, the length of the container and the longitudinal structure may be similar to that shown in FIG. 2, and need not be repeated here. However, to provide the greater capacity, the longitudinal side walls 142, 144 are formed into upper lateral extensions 160, 161 respectively. Thus, for example, the extension 160 includes an outer side wall 142A, the upper portion of which is formed into the double seal flange 114 for engaging and sealing with the correspondingly-curved peripheral seal flange 113 of the cover 111. The bottom of the extension 161 may be ribbed as at 163 similar to the ribs formed in the bottom wall 141; and those ribs may extend upwardly into the shorter side wall extensions, one of which is seen at 143A in FIG. 5.

In order to accomodate the cover to the increased lateral extension of the tray, the previously-described land 30 is extended laterally as shown at 130A in FIG. 5. Otherwise, the structure of the alternate embodiment of FIG. 5 is similar to that described in connection with the first embodiment.

In use, the surgical instrument or medical device desired to be sterilized is placed in the tray 12, resting on the upper surfaces 48 of the grooved bottom. In the embodiment of FIG. 5, the item to be sterilized may be rested, if it is large enough, on the bottoms of one or both of the side extensions 160, 161. The cover is then assembled to the tray, insuring full surface contact between the two cusps of the sealing flanges. To facilitate assembly, the fingers of one hand may engage the lower peripheral flange 55 of the seal flange 14 of the tray, while the thumbs press down on the curved seal portions 31, 32 of the cover. By continuing this action progressively throughout the periphery, a complete, continuous seal and a large contact area may be assured between the two seal flanges.

In order to provide an interference fit between the two serpentine sections of the respective flanges 13, 14, the curved seal portions 31, 32 of the flange 13 are made to the identical dimensions, including curvature, as the curved portions 45, 46 of the sealing flange 14. The nonwoven material is deformable to the extent that an interference fit can be achieved by using the closing motion described above, and the natural friction of the material insures that the cover will not be separated inadvertently from the tray, although the container may readily be opened in a manner to be described presently.

The present invention may be used in all the various current processes for sterilizing medical items. In subjecting the container and its contents to steam sterilization, it will be appreciated that there is line-of-sight permeability of the steam from all incident angles, unlike the limited access in the case of solid stainless steel walls of some prior sterilization trays or the "reusable" containers of the prior art described above. This is considered an important advantage in insuring complete and rapid sterilization of articles of all sizes and shapes.

Because of the low heat capacity of the nonwoven material, there is little or no condensation of the steam on the surface of the container. What little condensation might occur because of the mass and heat capacity of the article being sterilized accumulates in the trough formed in the bottom of the tray. Instrument contact with accumulated water is prevented because of the ribbed structure of the bottom wall 41 of the tray, the water collecting in the grooves between the ribs 46, and the instrument resting on the raised inner surfaces 48. The low heat capacity of the nonwoven fabric enables a person to remove the container almost immediately after sterilization and without fear of burn or discomfort. The container acts as a insulator against the heat of the sterilized item, if it is metal.

In addition to adding strength, the ribbing of the bottom of the tray has the further advantage of facilitating removal of the item after sterilization by means of forceps or the like while maintaining sterile technique. That is, even if the item is flat, forceps or other handling instruments can be used to engage the item by working the forceps into the grooved areas. In this connection, the elevated portions or cusps 48 act as set offs for the item being treated to facilitate grasping of the item for removal. These cusps further serve to promote circulation of steam to all surfaces of the item during sterilization and to provide ventilation and drying of the article after sterilization.

Handling of the container and contents is made easier due to the lighter weight of the nonwoven as well as the cooperative relation of the sealing flanges' acting as extensions or ledges for the fingers while the thumbs are placed in the end recesses 25, 26 to hold the cover in place and to stabilize the container and its contents.

Another important advantage of the invention is that it provides a means of insuring sterile conditions during presentation of the sterilized contents. For example, it may be desirable for a circulating nurse to present a medical instrument to a scrub nurse during procedural maneuvers. The circulating nurse may firmly grasp the tray in one hand by straddling the bottom wall 41 with that hand and grasping the longer (more closely spaced) opposing side walls 42, 44 with the thumb and fingers of the same hand, and by using the other hand to similarly grasp the body 15 of the cover 11 (that is, by straddling the top wall 16 of the cover with the other hand and grasping opposing side walls 17, 19 between the fingers and thumb of that hand). In this connection, the index finger of the hand grasping the cover may conveniently rest in one of the end recesses 25, 26 (see FIG. 1) to add further stability in handling.

With the tray and cover firmly grasped with the hands in opposing relation, it will be appreciated that the hands are fixed relative to the structure, and considering, for example, particularly FIG. 4, it will be understood that the thumb and fingers of both hands are isolated from the sealing surfaces even after the cover is removed from the tray, thereby maintaining sterility of the inner serpentine surfaces of the sealing flanges as well as the contents. The contents of the tray may then be presented with the hand grasping the tray, again without fear of contamination.

Because of the double seal and tortuous path defined by the sealing portions of the flanges 13, 14, and the continuous contact throughout, the structure of the present invention makes it possible to sterilize surgical or medical items well ahead of time and maintain that sterility because the tortuous path of the seal flanges maintains the bacterial barrier created by the structure.

The light weight of the nonwoven material, in contrast to prior stainless steel trays, affords greater flexibility and less likelihood of dropping the contents. The lid and tray maintain their semi-rigid nature due to the resin content of the nonwoven material and the structural rigidity designed into the members, as described above.

The present invention makes it possible to establish new, less complex sterile techniques in view of the continuous, maintained seal in a closed container provided by the instant invention, thereby insuring even safer operative procedures in the future.

The nonwoven container material preferably is treated with an agent to provide fluid repellency which characteristic is maintained even after sterilization. One suitable agent for making the nonwoven fluid repellent is available under the trademark "SCOTCHBAN" from 3M Co. of Minneapolis, Minn. The material may also be treated with a fixed antimicrobial agent to increase sterile storage time.

Various modifications may be designed into the structure of the illustrated embodiment, such as the use of temperature-sensitive ink to indicate when the container has gone through sterilization; the inclusion of a device (e.g., a frangible clip or wire, tape, etc.) which would bridge between the tray and the cover to indicate sterility and provide a visual indication if the container were opened after sterilization; and perhaps lining the tray with an inner layer of cushion material for shock absorbtion of implants, prosthetic devices, or delicate instruments.

Ohter contemplated modifications include forming the tray to accomodate special inserts or holders for sharp or delicate instruments. Additionally, if high security were desired after sterilization, a bead of adhesive (either contact or heat actuated) could be applied, for example, in the trough between cusps 45, 46 of the tray as seen in FIG. 2, to seal the tray and cover during sterilization and insure security thereafter until use.

Having thus disclosed alternate embodiments of the invention, persons skilled in the art will be able to modify certain of the structure which has been illustrated and to substitute equivalent materials for those illustrated, while continuing to practice the principle of the present invention. It is therefore intended that all such modifications and substitutions be covered as they are embraced within the spirit and scope of the appended claims.

We claim:

1. A sterilization container capable of withstanding steam sterilization without substantial change in physical properties comprising: a cover of nonwoven material and including a top, a plurality of sidewalls depending from said top, and a seal flange extending about the periphery of said cover side walls; and a tray of nonwoven material and including a bottom, a plurality of side walls extending upwardly of said bottom, and a seal flange extending about the periphery of said tray side walls; said sealing flanges of said cover and tray defining correspondingly curved paths in directions outward of their respective side walls and cooperating to form a continuous seal and define a tortuous path for providing a bacterial barrier when said cover and tray are assembled.

2. The article of claim 1 wherein said cover and tray each have four side walls, a pair of opposing side walls of each of said cover and tray being spaced such that a person may grasp the cover by straddling the top with one hand and gripping said pair of opposing cover side walls respectively with the fingers and thumb of said one hand, and said person may grasp the tray by straddling the bottom with the other hand and gripping said pair of opposing tray side walls respectively with the fingers and thumb of said other hand, characterized in that said hands are located remotely of the engaging surfaces of said seal flanges after the seal is broken to avoid inadvertent contamination of said seal during subsequent presentation of the sterilized items.

3. The article of claim 1 wherein said curved paths of said sealing flanges define a continuous serpentine path providing two sealing cusps arranged in tandem relation between the inner and outer boundaries of said sealing flanges.

4. The article of claim 3 characterized in that the respective sealing flanges of said cover and tray extend continuously respectively about the peripheries thereof and define extended areas in frictional engagement with each other.

5. The article of claim 4 characterized in that the opposing surfaces of said sealing flanges of said cover and tray are in continuous contact with each other substantially through the entire extension of said curved paths thereof.

6. The article of claim 5 wherein said curved portions of said sealing flanges of said cover and tray respectively are manufactured to the same dimensions to thereby insure an interference fit when the cover is sealingly assembled to said tray.

7. The article of claim 6 wherein the furthest peripheral portion of said flanges cooperate to define horizontally extending peripheral sealing flanges beneath and laterally outward of said tandem seal cusps.

8. The article of claim 1 wherein said bottom of said tray includes a plurality of elongated ribs defining raised interior portions for supporting an item placed therein and setting the same off relative to any moisture collected in the grooves between said ribs.

9. The article of claim 7 characterized in that said ribs continue into the adjacent side walls of said tray; and further comprising cross ribs extending transversely between adjacent longitudinal ribs for bracing the same.

10. The article of claim 8 wherein the top wall of said cover defines longitudinally extending ribs generally parallel to the ribs of said bottom of said tray.

11. The article of claim 9 wherein said top wall of said cover further define generally V-shaped ribs on opposing sides and opening toward said sides to define flat finger recesses adjacent opposite sides thereof; said V-shaped ribs uniting with said longitudinally extending ribs.

12. The article of claim 1 wherein said seal flanges extend outwardly of the associated side walls of said lid and tray to a sufficient distance to allow the fingers or thumb of a person to grasp the respective tray of lid without inadvertently contaminating the outermost portion of said lid.

13. The article of claim 1 further including first and second outwardly projecting lateral extensions of opposing side walls of said tray, the bottoms of said extensions being raised above the bottom of the main body portion of said tray to permit the hand of a person to firmly engage the central body portion by straddling the same with a hand and grasping the sides thereof firmly in opposing gripping relation of the fingers and thumb of said hand respectively beneath the lateral extension of said tray.

14. A sterilization container capable of withstanding steam sterilization procedures while maintaining semi-rigid structural integrity and without substantially diminishing the load-bearing capability thereof, comprising: a cover and a tray substantially entirely of nonwoven material characterized in being semi-rigid, water repellant and permeable to gas and steam, said cover defining a handleable body portion capable of being firmly grasped in one hand, and a serpentine seal flange extending continuously about the periphery of the lower edge of said body portion and characterized in that when said body portion is grasped by a hand, all portions of the hand are fixed and remotely located from the outermost portion of said sealing flange; said tray defining a handleable tray portion with a bottom and a plurality of side walls extending upwardly thereof, and a seal flange extending continuously about the periphery of the upper edge of said tray side walls; said seal flange of said tray continuously conforming to and engaging the peripheral seal flange of said cover, said seal flanges of said cover and tray cooperating to define a tortuous seal path for providing a bacterial barrier when the same are in assembled relation with each other.

15. The article of claim 12 wherein said cover and said tray have generally rectangular horizontal cross-sections including a pair of longer opposing side walls and a pair of shorter opposing side walls, the bottom of said tray defining a plurality of alternate ribs and grooves extending parallel to said longer side walls, the upper surfaces of said ribs defining set off support surfaces for supporting a medical items said groove providing moisture collection troughs.

16. The article of claim 15 wherein said seal flanges extend laterally outwardly of the respective side walls of said cover and tray to define an inner seal cusp and an outer seal cusp in tandem, and an outer peripheral skirt extending downwardly of said outer seal cusp.

17. The article of claim 15 wherein said seal flanges include a continuous circumferential horizontal peripheral flange extending outwardly of the lower portion of said skirt.

* * * * *